United States Patent [19]

Larsson et al.

[11] 4,361,484

[45] Nov. 30, 1982

[54] PROCESS FOR TREATING AND/OR REMOVAL OF SUBSTANCES FROM LIQUID, ESPECIALLY WHOLE BLOOD

[75] Inventors: Lars-Ake L. Larsson, Loddekopinge; Lars O. V. Naucler; Ulf T. G. Nylen, both of Lund, all of Sweden

[73] Assignee: Gambro AB, Sweden

[21] Appl. No.: 232,037

[22] PCT Filed: Jun. 11, 1979

[86] PCT No.: PCT/SE79/00132

§ 371 Date: Feb. 11, 1981

§ 102(e) Date: Jan. 9, 1981

[87] PCT Pub. No.: WO80/02805

PCT Pub. Date: Dec. 24, 1980

[51] Int. Cl.³ .................... B01D 13/00; B01D 31/00
[52] U.S. Cl. .................................. 210/632; 210/637; 210/651; 210/321.3; 210/433.2; 435/269; 435/288; 435/289
[58] Field of Search ........ 210/632, 637, 638, 644–646, 210/648–651, 669, 679, 691, 692, 694, 741, 790, 137, 266, 321, 433.2, 443, 927; 435/2, 174, 179, 180, 182, 269, 288, 289

[56] References Cited

U.S. PATENT DOCUMENTS

| | | | |
|---|---|---|---|
| 3,608,729 | 9/1971 | Haselden | 210/321.3 |
| 3,864,248 | 2/1975 | Granger et al. | 210/637 X |
| 4,013,564 | 3/1977 | Nose | 210/321.1 X |

FOREIGN PATENT DOCUMENTS

| | | | |
|---|---|---|---|
| 2225862 | 12/1973 | Fed. Rep. of Germany | 210/433.2 |
| 2558363 | 7/1977 | Fed. Rep. of Germany | 210/433.2 |
| 2270895 | 12/1975 | France | 210/321.1 |
| 2404439 | 4/1979 | France | 210/321.3 |
| 383258 | 6/1972 | Sweden | 210/433.2 |
| 373752 | 1/1975 | Sweden | 210/321.3 |
| 1491261 | 11/1977 | United Kingdom | 210/321.1 |

OTHER PUBLICATIONS

Robertson, C. R. et al., "LAR Separation Barriers and Their Application to Catalytic Reactor Design", Separation and Purification Methods, vol. 5, No. 2, pp. 301–332, (1976).

Thomas, D. et al., "Artificial Enzyme Membranes" in Methods in Enzymology, vol. 44, Immobilized Enzymes, K. Mosbach Editor, pp. 901–907, (1976), Academic Press.

Primary Examiner—David R. Sadowski
Attorney, Agent, or Firm—Lerner, David, Littenberg & Samuel

[57] ABSTRACT

A process for the treating of and/or removal of substances from a liquid, especially whole blood, via a semipermeable microporous membrane (13, 14, 15) through adsorption and/or biological reaction by means of a biologically active material. Said whole blood is exposed to pressure variations at the membrane surface in a way such that a penetrating fraction of said whole blood is flowing in an alternating flow path through the membrane walls for contacting said biologically active material.

Said biologically active material is asymmetrically immobilized in and on the surface of the side of said membrane that faces away from said whole blood. Alternatively, said biologically active material may be bound to an unsoluble matrix behind said membrane.

Said membrane is for example provided within a casing (7, 8, 9) comprising inlet (10) and outlet (11) for said whole blood. The space between said casing and said membrane is via a connecting nipple (12) in communication with for example an expansion chamber for the provision of pressure variations.

By means of the device (3) it is possible to perform said process in one and the same step and by means of one and the same pumping system.

34 Claims, 7 Drawing Figures

PROCESS FOR TREATING AND/OR REMOVAL OF SUBSTANCES FROM LIQUID, ESPECIALLY WHOLE BLOOD

TECHNICAL FIELD

This invention relates to a process for the treating of and/or removal of substances from a liquid via a microporous, semipermeable membrane through adsorption and/or biological reaction by means of a biologically active material. Furthermore, this invention relates to a device and a membrane for the realization of said process, and a process for immobilizing of a biologically active material on and/or in such a membrane.

Especially this invention is concerned with a process for the removal of substances from whole blood.

Examples of such substances are immune complexes of IgG- or IgA-type having molecular sizes within the range of from $20 \times 10^4$ to $10^6$ Daltons. Further examples are antibodies, for example immunoglobulins of IgG-, IgM- and IgA-types, and antigens, for example virus and DNA in systemic lupus erytematosis (SLE). Also harmful enzymes, for example some proteolytic enzymes which are detrimental to human organs, are examples of such substances in this especial context.

Even though the present invention will be described with particular reference to a process for the treating of and/or removal of substances from whole blood, so-called blood immunotherapy, it is to be understood that the invention is not restricted to only this particular field of use. In its broader sense the present invention may be applied to other liquids which are to be treated in the way specified in the preamble of claim 1.

BACKGROUND OF INVENTION

Substances, for example macromolecules, in whole blood are usually captured or transformed specifically.

For example it is required that the blood corpuscles are initially separated from the plasma which is then treated separately for the removal of said macromolecules. Then, said plasma is filtered in further separate steps to remove possible remaining harmful substances, whereafter said plasma is finally rejoined with said blood corpuscles and fed back to the source for said whole blood.

If a rapid process is desirable, said separation is performed through plasmapheresis based on a centrifuge step. A more simple process is however realized, if said separation of whole blood is performed by means of a microporous, semipermeable membrane filter.

Irrespective if said separation of whole blood is realized through centrifuging or by means of a microporous, semipermeable membrane filter, two separate pumping systems are required in this known technique for the realization of said process, i.e. a pumping system for said whole blood and a pumping system for said plasma. The reason for this inconvenience is primarily that said process necessarily must be divided into more separate steps, as described hereinabove.

An object of the present invention thus is therefore to avoid said inconvenience in the known technique and to provide a process which does not require a dividing into separate steps for the treating of and/or removal of substances from the liquid, especially whole blood, and which therefore does not require two pumping systems.

Another object is to provide a device and a membrane for the realization of said process.

A further object is to provide a process for the immobilizing of biologically active material on and/or in such a membrane.

Other objects and advantages of the present invention will be apparent from the following description.

DESCRIPTION OF INVENTION

According to the present invention there is provided a process for the treating of and/or removal of substances from a liquid, especially whole blood, via a microporous, semipermeable membrane through adsorption and/or biological reaction by means of a biologically active material. Said process is characterized in that a penetrating fraction of said liquid is forced to flow in an alternating path through said microporous membrane in each direction for contacting said biologically active material.

According to the present invention there is furthermore provided a device for the treating of and/or removal of substances from a liquid, especially whole blood, via a microporous semipermeable membrane through adsorption and/or biological reaction by means of a biologically active material. Said device is characterized in comprising means for the realization of an alternating flow of a penetrating fraction of said liquid through said membrane in each direction.

Furthermore, there is provided a microporous semipermeable membrane for the treating of and/or removal of substances from a liquid, especially whole blood, through adsorption and/or biological reaction by means of a biologically active material. Said membrane is characterized in that said biologically active material is immobilized in the pores and/or on the surface of the side of said membrane which is adapted to be faced away from said liquid.

Furthermore, there is provided a process for the immobilizing of IgG (biologically active material) on and/or in a microporous semipermeable membrane of amine substituted polyamide via glutardialdehyde. Said process is characterized in that one surface of said membrane is treated with a solution of glutardialdehyde in phosphate buffer; the so treated membrane is rinsed with distilled water and then sucked relatively dry; that IgG, dissolved in phosphate buffer, is poured over said membrane to cover same; that the system is evacuated; that the coupling is allowed to proceed; and in that said membrane finally is carefully rinsed with water.

Furthermore, there is provided a process for the immobilizing of protein A (biologically active material) on and/or in a microporous, semipermeable membrane of cellulose acetate. Said process is characterized in that one surface of said membrane is treated with chloroacetic acid for coupling of carboxymethyl groups to said membrane; that said membrane is dried and then transferred into a degassed solution of phosphate buffer containing 1-ethyl-3(3-dimethyl-aminopropyl)carbodiimide; that the reaction is allowed to proceed, whereafter said membrane is washed with phosphate buffer to removing excess of 1-ethyl-3(3-dimethylaminopropyl) carbodiimide; that protein A is provided to cover said membrane which then is reacted with said protein; and in that said membrane finally is washed with water.

In the particular case where said liquid is constituted by whole blood, said biologically active material may be chosen from the group consisting of the following proteinaceous material: antibodies, antigens, enzymes, protein A and the like, for example killed bacteria or fragment thereof.

The choice of proteinaceous material is determined primarily of the type of substance that is to be treated and/or removed.

For example, if antibodies or complexes of antibodies and antigens, so-called immune complexes, are to be removed, protein A is preferably chosen, which preferably captures immune complexes of IgG-type, IgG and some IgM and IgA. Alternatively certain membrane protein from streptococci may be chosen, which relatively specifically binds to IgA and immune complexes thereof. A further alternative may be specific antigen in order to eliminate antibodies which are harmful to tissue, for example in transplantations.

If antigens, for example a virus or DNA in SLE, are to be removed, then it is convenient to choose an antibody which specifically binds to such antigens. Also antibodies or other fix adsorbents may be chosen to eliminate harmful enzymes, for example certain proteolytic enzymes which are detrimental to human organs.

Enzymes which perform biological reactions which the body does not manage to handle owing to any enzyme deficiency disease, constitutes examples of further biological material which can be used according to this invention.

The membrane according to the present invention may consist of any suitable blood compatible material which is able to bind to the biologically active material. Examples of such suitable material are regenerated cellulose, cellulose acetate, non-woven acrylic copolymer, polysulphon, polyethersulphon, polyacrylonitrile, polyamide and the like. The pores of said membrane are usually of the magnitude of order of 0.01 to 0.8 microns, preferably 0.15 to 0.45 microns.

Said membrane may be either in planar form or in form of one or more hollow fibers. In said planar form said membrane has the biologically active material bound in the pores and/or on the surface of the side of said membrane that faces away from the whole blood. When the membrane is in the form of hollow fibers, said biologically active material preferably is bound in the pores and/or on the surface of the outer side of said fiber or fibers. The whole blood is in this case adapted to flow through the longitudinal void in said fibers.

Alternatively, said membrane may be composed of two membrane halves which are mechanically generally identic to each other but which chemically may be built up of different material. In this case it is enough if only the membrane half that faces away from the whole blood is able to bind to the biologically active material. For example, said membrane halves may be provided in an abutting relationship to each other, wherein the biologically active material preferably is bound in the pores and on both surfaces of the membrane half that faces away from the whole blood.

Irrespective of the outer shape or chemical or mechanical constitution of said membrane, said biologically active material (for example protein A, antibodies, antigens, enzymes) must be immobilized in said membrane in such a way that the surface of said membrane that faces towards the whole blood is free of "reagent". This is to avoid contact between blood corpuscles and the reagent and thereby pyrogen and/or anaphylactic reactions. Thus it is a form of a symmetric immobilization, where on one surface of said membrane as well as in the pores thereof said biological active material has been immobilized. The advantage of immobilizing within the pores on said membrane is that the active microscopic surface may be manifolded (>1000) compared to the macroscopic surface.

Through the asymmetric immobilizing of said biologically active material the diffusion distance from the blood to the biologically active material is very short ($\leq 0.30$ mm; thickness of membrane). Grace to this short distance a somewhat oscillating pressure wave is enough for providing desired transport of high molecular substances from the blood to said biologically active material.

Alternatively, said biologically active material may be bound to an unsoluble matrix behind said membrane. The treating process is yet similar, but since the necessary diffusion distance is about 10 times longer, it may be necessary to arrange a somewhat more real flow through said membrane.

Irrespective of whether the biological material is immobilized in the pores or an unsoluble matrix behind said membrane is used for immobilizing said active material, the immobilizing procedure must be so performed that said active material cannot be broken away. This means that covalent coupling is the most safe immobilization. What exact type of covalent coupling that is to be used depends on the choice of membrane material and the type of used biologically active material.

According to a preferred embodiment of the present device the microporous semipermeable membrane is used in the form of flat foils. Said foils are provided in pairs between distance plates and together with said distance plates clamped within a casing comprising inlet and outlet for the whole blood. This construction differs from a so-called "plate kidney", which is known to the person skilled in the field of dialysis, primarily through the lack of corresponding inlet and outlet for dialysis solution. A more detailed description of this construction is therefore hardly necessary in this context. The whole blood to be released from substances, is pumped from for instance a patient into said casing through said inlet and is distributed in a convenient way through the spaces between said membrane foils being provided in pairs. During the passage through said spaces said whole blood is exposed to pressure variations in a manner so that only a penetrating fraction of said whole blood is caused to flow in an alternating path through the respective membrane foil in each direction for contacting said immobilized biologically active material. In this way said whole blood will be partly separated, partly treated within one and the same casing in one and the same step. Since the biologically active material is immobilized in the part of membrane that faces away from said whole blood said whole blood will not come into contact with said material. Consequently, any following separate filtering of said whole blood therefore is not necessary.

The means for the realization of said pressure variations may for instance be made up of an expansion chamber in fluid communication with the spaces between said membrane pairs and distance plates, respectively, which alternatingly is exposed to overpressure and underpressure in relation to the pressure of said whole blood.

According to another preferred embodiment of the present device said microporous semipermeable membrane is in the form of individual fibers which may be provided into bundles and encapsulated within one and the same casing comprising inlet and outlet for said whole blood. The ends of said fibers are glued by means of a suitable binder in a way such that said individual fibers are retained essentially parallel within said casing. One end of said fibers or bundles of fibers is provided in communication with said inlet, while the opposite end is provided in communication with said outlet. Said whole blood is pumped into said casing through said inlet and through the longitudinal void of said fibers and out of said casing through said outlet. During said passage through said casing said whole blood, as described above, is exposed to said pressure variations, such that only a penetrating fraction of said whole blood is caused to flow in an alternating path through the fiber walls in each direction for contacting with said biologically active material. The means for the realization of said pressure variations may again be made up of an expansion chamber in communication with the space between said individual fibers and bundles of fibers, respectively. Again, the separation of whole blood as well as the capturing of said substances on the biologically active material is provided in a single step. Any following filtering of said whole blood for the removal of possible harmful residues is neither requested, since said filtering is automatically achieved through the passage of said plasma through said fiber walls.

Said pressure variations may vary from −200 to −200 mmHg, preferably from −100 to +100 mmHg. The longer the diffusion distance for the blood, for example if the biologically active material is bound to an unsoluble matrix behind said membrane, the higher compensating pressure variations are required to achieve the desired separation effect. In a corresponding way the frequency of said pressure variations may vary from about 0.05 up to about 10 Hz, preferably 0.5 to 1 Hz.

BRIEF DESCRIPTION OF THE DRAWINGS

The present invention will be described with reference to preferred embodiments of as well the process, the device as the microporous semipermeable membrane.

In FIGS. 5-7 the following symbols have been used:
o = biologically active material
⊙ and ⌀, respectively = granules comprising biologically active material.

THE MOST PREFERRED EMBODIMENT OF THE INVENTION

Figure 1:
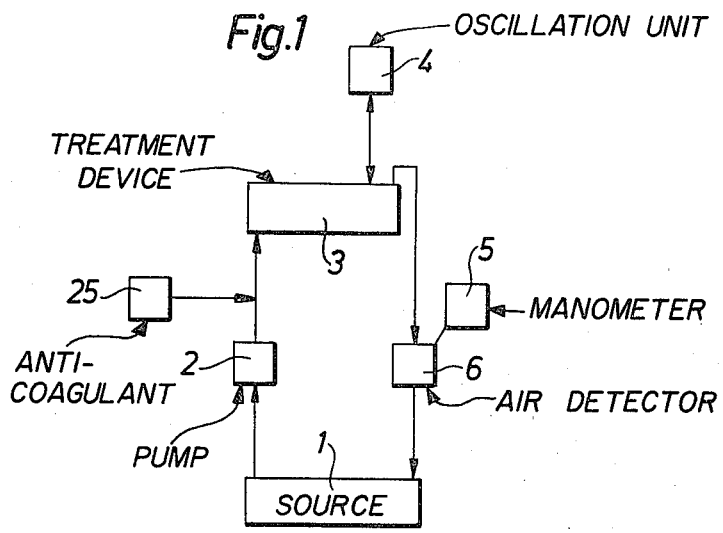
FIG. 1 is a schematic flow diagram showing the mode of carrying out the present process.

In order to remove for example antibodies or complexes of antibodies and antigens, so-called immune complexes, from a liquid, especially whole blood, said whole blood is withdrawn from a source 1 (FIG. 1), for example a patient, by means of a pump 2. Said pump 2, which may be a conventional blood pump, pumps said whole blood into the present device, generally designated 3. In said device said whole blood is exposed to pressure variations of the magnitude of order of from −200 to +200 mmHg, preferably from −100 to +100 mmHg, by means of an oscillation unit 4 which provides said pressure variations with a frequency of 0.05-10 Hz, preferably 0.5-1 Hz. In this way a penetrating fraction of said whole blood, i.e. the plasma, will flow in an alternating path through the walls of semipermeable microporous membranes in each direction, which are provided in the device 1, for contacting said biologically active material, for example protein A. For more detailed information as regards said membranes reference is made to the following description. Said whole blood, which has passed through the device 3, is then pumped back into said patient 1 via a manometer 5 and an air detector 6. As well said monometer 5 as said air detector 6 are conventional in the field and need therefore not be described more in detail. The addition of anticoagulantia, as shown at 25, such as heparin, may be a pump or similar construction which in a well-known manner adds said heparin.

Figure 2:
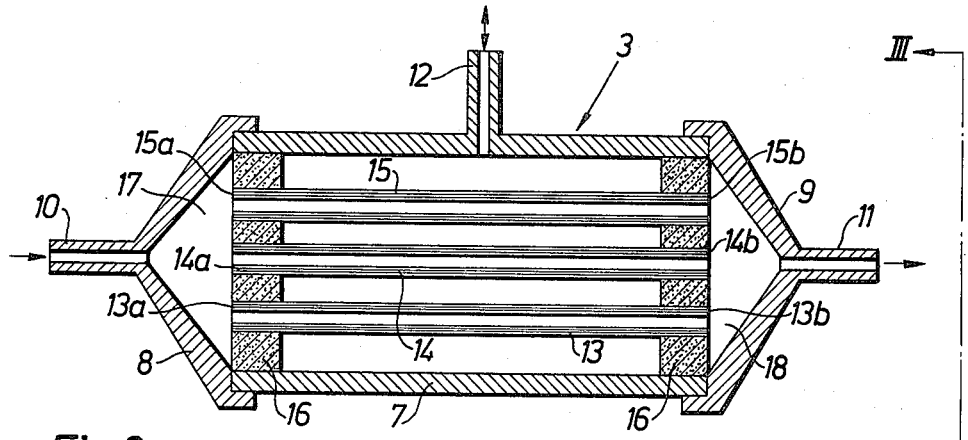
FIG. 2 is a longitudinal cross-section through a preferred embodiment of the present device, including microporous, semipermeable membranes in the form of fibers which are encapsulated within one and the same casing comprising inlet and outlet for the whole blood.
Figure 3:
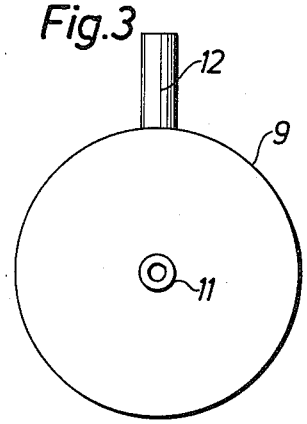
FIG. 3 is an end view of the device of FIG. 2.

According to a preferred embodiment of the present invention the device 3, as shown in FIGS. 2 and 3, consists of an essentially cylindrical intermediate part 7, both ends of which are closed by means of two identic conically shaped lids 8 and 9, respectively, while forming inlet 10 and outlet 11, respectively. Said intermediate part 7 is provided with a connecting nipple 12 for communication with said oscillation unit 4, as schematically shown by means of the two-headed arrow in FIG. 2.

The device according to FIG. 2 comprises microporous semipermeable membranes in the form of individual fibers 13-15, preferably of cellulose acetate. The ends of said fibers are glued by means of a suitable binder 16 in a manner such that said individual fibers 13-15 are essentially parallel within said casing. One end 13a, 14a, 15a of said fibers is provided in communication with said inlet 10, while the opposite ends 13b, 14b, 15b are provided in communication with said outlet 11. Said whole blood is pumped into the device 3 through said inlet 10 and is distributed into the space 17 between the fiber ends 13a-15a and the conical lid 8, such that essentially uniform portions of the entering whole blood will pass through the longitudinal void of each of said fibers 13-15. After the passage through said fibers said whole blood is collected in the space 18 between the fiber ends 13b-15b and the conical lid 9 and flows in a concentrated flow out of the device 3 through said outlet 11.

Even if only three individual fibers 13-15 are shown in FIG. 2, said number may vary. For example said individual fibers may be provided in the form of bundles or bunches.

Figure 4:
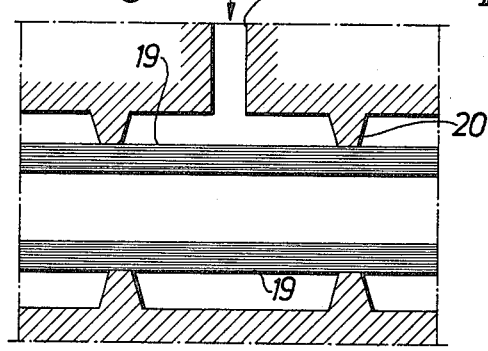
FIG. 4 is part of a longitudinal cross-section through another preferred embodiment of the present device, wherein said microporous semipermeable membrane is in the form of individual fibers or thin-walled tubes.

The embodiment shown in FIG. 4 differs from that of FIGS. 2 and 3 primarily in that the microporous semipermeable membrane is constituted by one individual fiber 19. To support said fiber 19 the device comprises heads or concentric flanges 20 which are adapted to abut against the outer wall of said fiber.

Figure 5:
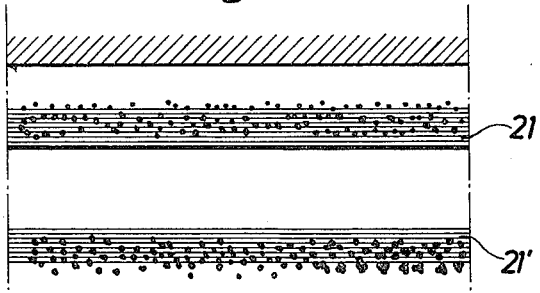
FIGS. 5-6 show preferred embodiments of the microporous, semipermeable membrane according to the present invention, comprising immobilized biologically active material.
Figure 6:
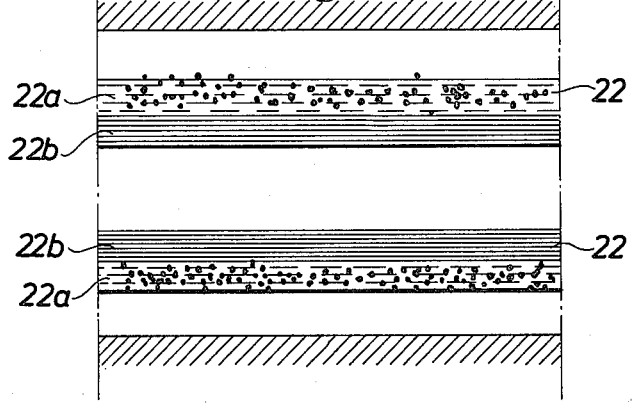
Figure 7:
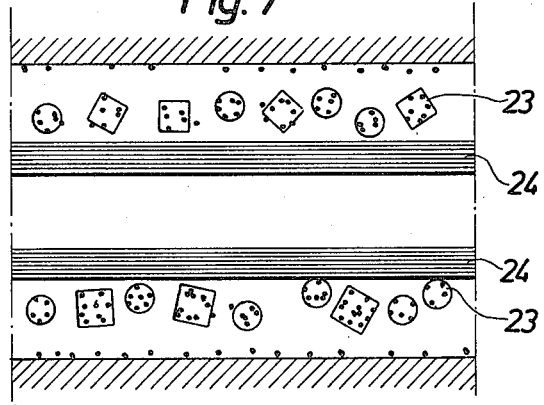

In FIGS. 5-7 different principles of immobilizing of said biologically active material are shown. In FIG. 5 said material is immobilized in and on the outer surfaces of flat membranes 21, 21'. In FIG. 6 the membrane 22 consists of two separate membrane halves 22a, 22b in an abutting relationship to each other. The biologically active material is immobilized on and in only the outer membrane half 22a. In FIG. 7 the biologically active material is received in granules 23 which are freely floating in the space around said microporous semipermeable membrane 24.

The following examples will illustrate concrete processes for coupling of said biologically active material to the present membrane.

EXAMPLE 1

In this example immobilizing of IgG to a polyamide membrane (nylon) is realized.

Amine substituted nylon membrane is manufactured as follows:

1. Said polyamide membrane is washed with 10% solution of Duponol RA (detergent) and is rinsed with distilled water and dried.
2. Triethyloxoniumtetrafluoroborate in dichloromethane was sucked into an evacuated vessel, wherein the membrane was applicated.
3. After 60 seconds the reagent solution was sucked off.
4. The membrane was rinsed through the so-called suction process with two portions of dichloromethane.
5. 1,6-diaminohexane was sucked into said reaction vessel and reacted with the activated groups of said membrane during 30 minutes at room temperature.
6. Finally, the membrane was flushed with distilled water during 24 hours and dried.

Coupling of IgG to the so treated membrane

In this example IgG was immobilized on and in the so treated membrane via glutardialdehyde. The membrane was therefore treated with 2.5% solution of glutardialdehyde in 0.1 M phosphate buffer at pH=6.8. Then the membrane was amply rinsed with distilled water and sucked dry.

IgG, dissolved in 0.1 mM phosphate buffer (4° C.) at pH=6.0 was poured over the membrane, so that this was covered. The system was evacuated during 30 minutes, whereafter the coupling was allowed to proceed during further 15 hours at 4° C.

Not coupled IgG was collected with the first rinsing water in an ion exchanger. The membrane was carefully rinsed with water, whereafter it was ready to be applicated in the present device.

EXAMPLE 2

In this example protein A was immobilized on a cellulose membrane.

In a first step carboxymethyl groups were coupled to a membrane washed with an alcohol. This was realized in that the membrane material was treated with chloroacetic acid.

The membrane was dried, while being careful so as to avoid formation of cracks. 0.2 M phosphate buffer at pH 4.75 was degassed. 1-ethyl-3(3-dimethylaminopropyl)-carbodiimide (EDC) was added, such that the alcoholic concentration of this substance was 0.1 M. The membrane was then transferred into said degassed EDC solution. The reaction was allowed to proceed during 30 minutes at room temperature. Warm phosphate buffer of pH=7.0 was used to wash said membrane free of excess of EDC.

Protein A in a concentration of 2 mg/ml was caused to cover said membrane. The membrane was then allowed to react with said protein during 24 hours at 4° C. Finally, the membrane was washed and was then ready to be applied in the present device.

INDUSTRIAL APPLICABILITY

The present process is especially, though not exclusively, useable for the treating of and/or removal of substances, such as enzymes, antigens and/or antibodies from whole blood. Said whole blood is pumped from for example a patient into a treating unit comprising a microporous semipermeable membrane having pores of 0.01–0.8 microns, preferably 0.15–0.45 microns. During the passage through the treating unit said whole blood is exposed to pressure variations (for example from −200 to +200 mmHg, preferably from −100 to +100 mmHg), whereby a penetrating fraction of said whole blood, i.e. the plasma, is caused to flow in an alternating path through the membrane wall in each direction for contacting the biologically active material.

Said biological active material may for example be antibodies, antigens, enzymes, protein A etc., for example killed bacteria or fragments thereof. The choice of biologically active material is determined primarily by the type of substances that are to be removed.

Suitable materials for the membrane are regenerated cellulose, cellulose acetate, non-woven acrylic copolymer, polysulphone, polyether sulphone, polyacrylonitrile, polyamide and the like. The biologically active material is immobilized in the pores and/or on the surface of the side of said membrane that faces away from said whole blood. Alternatively said biologically active material may be bound to an unsoluble matrix behind the membrane. Thereby the blood corpuscles are prevented from contacting said active material.

After the passage through the treating unit said whole blood is reinserted in the patient.

Through the above construction of the microporous membrane, i.e. asymmetric immobilizing of said biologically active material, said whole blood need not be exposed to any following filtering for removing possible remaining harmful residues. As well the separation as the removal of said substances can thereby be performed in one and the same step.

We claim:

1. A process for treating a liquid to remove a substance therefrom comprising the steps of providing a chamber including a microporous semi-permeable membrane filter, a first liquid containing said substance to be removed in direct contact with one side of said membrane filter, and a second fluid in direct contact with the other side of said membrane filter, wherein at least a portion of said first liquid containing said substance is capable of penetrating said membrane filter, wherein a substance removal agent is immobilized with regard to said membrane such that the substance removal agent contacts said penetrating portion of said first liquid but does not directly contact said first liquid itself, and wherein said substance removal agent is selected from the group consisting of material capable of adsorbing said substance, material capable of reacting biologically with said substance to remove said substance, and mixtures of such materials; withdrawing a portion of said second fluid from said chamber to create a first predetermined pressure for said second fluid below that of the first liquid; and supplying said second fluid to said chamber to create a second predetermined pressure for said second fluid above that of the first liquid; wherein said withdrawing and supplying steps cause said penetrating portion of said first liquid to flow in an alternating path in the pores of said membrane filter to effect contacting of said penetrating portion containing said substance with said substance removal agent.

2. A process according to claim 1, wherein said substance removal agent is immobilized on the outer surface of said membrane filter external to said first liquid to be treated.

3. A process according to claim 1, wherein said substance removal agent is immobilized in the pores of said membrane filter external to said first liquid to be treated.

4. A process according to claim 1, wherein part of said penetrating portion of said first liquid passes through said membrane filter and is collected in said second liquid.

5. A process according to claim 4, wherein said second fluid comprises said penetrating portion of said first liquid which passes through said membrane filter.

6. A process according to claim 2, 3 or 5 wherein said substance removal agent is a biologically active proteinaceous material.

7. A process according to claim 2, 3 or 5 wherein said substance removal agent is selected from the group consisting of antibodies, antigens, enzymes, protein A, killed bacteria and fragments thereof, and mixtures thereof.

8. A process according to claim 2, 3 or 5 wherein the alternating of the flow of said penetrating fraction through the microporous semi-permeable membrane filter is accomplished by exposing said second fluid to pressure variations of from about $-100$ to about $+100$ mmHg.

9. A process according to claim 2, 3 or 5 wherein the alternating of the flow of the penetrating portion through said microporous semi-permeable membrane filter is accomplished by exposing said second fluid to pressure variations of from about $-200$ to about $+200$ mmHg.

10. A method according to claim 9, wherein said pressure variations are applied at a frequency of from about 0.05 to about 10 Hz.

11. A method according to claim 9, wherein said pressure variations are applied at a frequency of from about 0.5 to about 1 Hz.

12. A process according to claim 1, wherein said substance removal agent is immobilized in a second separate microporous semi-permeable membrane on the side of said membrane filter external to said first liquid to be treated.

13. A process according to claim 12, wherein said membrane and said second separate microporous semi-permeable membrane are in an abutting relationship with each other.

14. A process according to claim 1, wherein said withdrawing and supplying steps are continuously alternately performed.

15. A process according to claim 1, wherein said first liquid is whole blood.

16. A process according to claim 1, wherein said second fluid is a dialysate liquid.

17. A process according to claim 1, wherein said substance removal agent is bound to a matrix insoluble in said second fluid and said insoluble matrix is contained in said second fluid.

18. A device for treating a liquid to remove a substance from said liquid, said device comprising a chamber; a microporous semi-permeable membrane filter arranged in said chamber so that a first liquid containing said substance to be removed contacts one side and a second fluid contacts the other side of said microporous semi-permeable membrane filter, wherein said membrane filter is structured so that at least a portion of said first liquid containing said substance is capable of penetrating said membrane filter; a substance removal agent in said chamber immobilized so that said substance removal agent cannot pass through said membrane filter so as to contact said first liquid but can contact said penetrating portion of said first liquid, wherein said substance removal agent is selected from the group consisting of material capable of adsorbing said substance, material capable of reacting biologically with said substance, and mixtures of such materials; means for introducing said second fluid to said chamber so that said second fluid contacts the other side of said membrane filter; means for alternately withdrawing said second fluid from and supplying second fluid to said chamber so as to cause said penetrating portion of said first liquid to flow in an alternating path in the pores of said membrane filter to effect contacting of said penetrating portion containing said substance with said substance removal agent.

19. A device according to claim 18, wherein said substance removal agent is bound to a matrix insoluble in said second fluid and wherein said insoluble matrix is contained in said chamber on said other side of said membrane filter.

20. A device according to claim 18, wherein said substance removal agent is immobilized on the surface of said membrane filter external to said first liquid to be treated.

21. A device according to claim 20, wherein said substance removal agent is immobilized on said surface by covalent bonding to said membrane filter.

22. A device according to claim 18, wherein said substance removal agent is immobilized in the pores of said membrane external to said liquid to be treated.

23. A device according to claim 22, wherein said substance removal agent is immobilized in said pores of said membrane filter by covalent bonding to said membrane filter.

24. A device according to claim 20, 22 or 19 wherein said substance removal agent is a biologically active proteinaceous material.

25. A device according to claim 20, 22 or 19 wherein said substance removal agent is selected from the group consisting of antibodies, antigens, enzymes, protein A, killed bacteria and fragments thereof, and mixtures thereof.

26. A device according to claim 20, 22 or 19 wherein said microporous semi-permeable membrane filter comprises a material selected from the group consisting of regenerated cellulose, cellulose acetate, non-woven acrlic copolymer, polysulfone, polyether sulfone, polyacrylonitrile, polyamide and mixtures thereof.

27. A device according to claim 20, 22 or 19 wherein said membrane filter has pores of from about 0.01 to about 0.8 microns.

28. A device according to claim 20, 22 or 19 wherein said membrane filter has pores of from about 0.15 to about 0.45 microns.

29. A device according to claim 20, 22 or 19, wherein said means for alternately supplying said second fluid to and withdrawing said second fluid from said chamber is means for exposing said second fluid to pressure variations of from about $-200$ to about $+200$ mmHg.

30. A device according to claim 29, wherein said means for exposing said second fluid to pressure variations provides pressure variations with a frequency of from about 0.05 to about 10 Hz.

31. A device according to claim 29, wherein said means for exposing said second fluid to pressure variations provides pressure variations with a frequency of from about 0.5 to about 1 Hz.

32. A device according to claim 20, 22 or 19, wherein said means for alternately supplying said second fluid to and withdrawing said second fluid from said chamber is means for exposing said second fluid to pressure variations of from about $-100$ to $+100$ mmHg.

33. A device according to claim 18, wherein said substance removal agent is immobilized in a second separate microporous semi-permeable membrane on the side of said membrane filter opposite said liquid to be treated.

34. A device according to claim 33, wherein said membrane filter and said second separate microporous semi-permeable membrane are in an abutting relationship with each other.

* * * * *

UNITED STATES PATENT AND TRADEMARK OFFICE
CERTIFICATE OF CORRECTION

PATENT NO. : 4,361,484
DATED : November 30, 1982
INVENTOR(S) : Larsson et al.

It is certified that error appears in the above-identified patent and that said Letters Patent are hereby corrected as shown below:

Column 5, line 25, "-200" should read --+200--.

Signed and Sealed this

Seventeenth Day of May 1983

[SEAL]

Attest:

DONALD J. QUIGG

Attesting Officer

Acting Commissioner of Patents and Trademarks